United States Patent
Arens et al.

(10) Patent No.: US 11,730,624 B2
(45) Date of Patent: Aug. 22, 2023

(54) TWO-POINT AND MULTIPLE-POINT SPOT HEATING AND COOLING

(71) Applicant: THE REGENTS OF THE UNIVERSITY OF CALIFORNIA, Oakland, CA (US)

(72) Inventors: Edward Arens, Berkeley, CA (US); Hui Zhang, Moraga, CA (US); Davide Filingeri, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 698 days.

(21) Appl. No.: 16/795,151

(22) Filed: Feb. 19, 2020

(65) Prior Publication Data

US 2020/0268551 A1   Aug. 27, 2020

Related U.S. Application Data

(63) Continuation of application No. PCT/US2018/048895, filed on Aug. 30, 2018.
(Continued)

(51) Int. Cl.
*A61F 7/02* (2006.01)
*A61F 7/00* (2006.01)

(52) U.S. Cl.
CPC ........ *A61F 7/02* (2013.01); *A61F 2007/0034* (2013.01); *A61F 2007/0035* (2013.01);
(Continued)

(58) Field of Classification Search
CPC ...... A61F 2007/0246; A61F 2007/0295; A61F 7/00; A61F 7/02; A61H 2201/02;
(Continued)

(56) References Cited

U.S. PATENT DOCUMENTS

2006/0195168 A1* 8/2006 Dunbar .............. A61N 1/36021
607/108
2013/0001212 A1   1/2013 Mangoubi
(Continued)

FOREIGN PATENT DOCUMENTS

WO   2013124866 A2   8/2013
WO   2016049563 A1   3/2016
(Continued)

OTHER PUBLICATIONS

ISA/KR, Korean Intellectual Property Office (KIPO), International Search Report and Written Opinion dated Mar. 12, 2019, related PCT international application No. PCT/US2018/048895, pp. 1-15, claims searched, pp. 16-20.

*Primary Examiner* — Tigist S Demie
(74) *Attorney, Agent, or Firm* — O'Banion & Ritchey LLP; John P. O'Banion (57) ABSTRACT

Apparatus and methods for producing thermal comfort using two point or multipoint heating or cooling that is applied to portion of a human body part to produce a warm or cool sensation over a larger area than that where the heating or cooling is directly applied. The body is induced to heat or cool itself by adjusting its neutral temperature setpoints. Increased warming perception from two-point, multipoint, and switching point stimulation causes downward adaptation in the neutral skin temperature of the user. Because spot heating and cooling sources operate at higher temperature differences from the skin than do area sources, they create a stronger perceived thermal sensation for the same power consumption. Point heating or cooling, rather than whole-area heating, can result in power savings and cost savings while improving occupant comfort.

9 Claims, 4 Drawing Sheets

Related U.S. Application Data (60) Provisional application No. 62/551,860, filed on Aug. 30, 2017.

(52) U.S. Cl.
CPC .............. *A61F 2007/0047* (2013.01); *A61F 2007/0093* (2013.01); *A61F 2007/0094* (2013.01); *A61F 2007/0095* (2013.01); *A61F 2007/0226* (2013.01); *A61F 2007/0228* (2013.01); *A61F 2007/0246* (2013.01); *A61F 2007/0295* (2013.01)

(58) Field of Classification Search
CPC .... A61H 2201/0228; A61H 2201/0285; A61H 2201/1635; A61H 2201/164; A61H 2201/50; A61H 39/06
See application file for complete search history.

(56) References Cited

U.S. PATENT DOCUMENTS

| | | | | |
|---|---|---|---|---|
| 2015/0230524 | A1* | 8/2015 | Stevens | H05B 1/02 |
| | | | | 219/494 |
| 2017/0135855 | A1* | 5/2017 | Stefan | A61B 90/98 |
| 2017/0209301 | A1* | 7/2017 | DeSeve | A41D 1/005 |
| 2019/0200886 | A1* | 7/2019 | Welsh | A61B 5/25 |

FOREIGN PATENT DOCUMENTS

| | | | |
|---|---|---|---|
| WO | 2016160691 | A1 | 10/2016 |
| WO | 2019046605 | | 3/2019 |

\* cited by examiner

TWO-POINT AND MULTIPLE-POINT SPOT HEATING AND COOLING

CROSS-REFERENCE TO RELATED APPLICATIONS

This application claims priority to, and is a 35 U.S.C. § 111(a) continuation of, PCT international application number PCT/US2018/048895 filed on Aug. 30, 2018, incorporated herein by reference in its entirety, which claims priority to, and the benefit of, U.S. provisional patent application Ser. No. 62/551,860 filed on Aug. 30, 2017, incorporated herein by reference in its entirety. Priority is claimed to each of the foregoing applications.

The above-referenced PCT international application was published as PCT International Publication No. WO 2019/046605 on Mar. 7, 2019 and republished on May 2, 2019, which publications are incorporated herein by reference in their entireties.

STATEMENT REGARDING FEDERALLY SPONSORED RESEARCH OR DEVELOPMENT

This invention was made with Government support under DE-AR0000529, awarded by the U.S. Department of Energy. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to environmental conditioning systems and methods for buildings, and more particularly to personal comfort systems (PCS) that provide control over the thermal comfort of individual occupants, which can substantially reduce the energy and economic costs of cooling and heating buildings and can greatly increase occupant comfort under both cooling and heating conditions.

2. Background Discussion

Providing an acceptable indoor environment is one of the primary functions of buildings since the environment affects occupant satisfaction, health, and productivity. Air conditioning systems are generally used to control the climate within a building or sections of a building by distributing temperature modified air from a conditioner to a specific set of outlet locations in the interior of the budding. Conventional climate conditioning of building interiors is energy-intensive and generally directed to conditioning space rather than to directly meeting the individual thermal requirements of each occupant.

Office occupant surveys have shown that thermal discomfort is a major cause of dissatisfaction with office environments. There are many reasons for thermal dissatisfaction in buildings (e.g., overcooling or overheating). One fundamental reason is the current practice of attempting to deliver uniform thermal conditions based on universal rules, without accounting for individual differences in comfort requirements.

The thermal comfort of occupants is of great importance because it drives the patterns of operation of HVAC (heating, ventilating, and air conditioning) systems, which can often account for 50% of building energy consumption in developed countries. The challenge with conventional climate conditioning systems is that there is only one thermostat provided to serve multiple occupants and consequently individuals are not able to set the temperature according to their comfort requirements.

Local temperatures that are experienced by individual occupants may also vary across different parts of the building as well as vary within the same climate conditioned zone. Such variations are often not captured in conventional HVAC systems as most buildings only have one temperature measurement and thermostat setting per zone.

Accordingly, the temperature at different floors, zones or locations within a building cannot be accurately controlled by a single thermostat. Although sophisticated computer controlled heating and cooling systems are possible, uniform temperature control within floors, zones or rooms of a building may not be comfortable to individual occupants within those areas.

Thermal comfort is a subjective phenomenon that may be influenced by a range of factors, and it can differ widely between individuals. It is therefore unreasonable to expect every occupant to be satisfied in a uniformly conditioned space even if the climate conditions meet current standards. The thermal sensations experienced by an occupant are dependent on a number of environmental (air temperature, radiant temperature, air speed, humidity) and personal (metabolic rate, clothing insulation) factors.

Occupants often have different thermal preferences even when they are all exposed to the same temperature conditions. The perception of what is a comfortable environment is often not the same between individuals with some preferring a slightly warmer work environment and others preferring a slightly cooler environment. Differences in comfort preferences can lead to conflicts among occupants over thermostat setpoints in shared spaces and ultimately cause dissatisfaction with their environment.

The ultimate goal for improved building operation is to simultaneously improve both system energy efficiency and occupant thermal comfort performance. However, this is still viewed as a mutually exclusive tradeoff where only one can improve at the expense of the other.

Accordingly, there is a need for a system that provides individualized comfort control for occupants of a building room, cubicle or other area and improve the overall satisfaction of the occupants while conserving energy by reducing air-conditioner or heater usage.

BRIEF SUMMARY

Current indoor climate standards for buildings have been set to achieve a steady state heat balance or "neutrality"

using air conditioned by the building's HVAC system, with resolution down to the zone level where the temperature is controlled by a thermostat. The thermal comfort of the occupants is assumed or predicted based on conditioned air to body heat transfer. However, it has been recognized that the condition or experience of thermal comfort is more complex than the steady-state heat balance adopted as the standard in the art.

Thermal comfort of a building occupant is affected by several variables including environmental (air temperature, radiant temperature, air speed, humidity) and personal (metabolic rate, clothing insulation, thermal adaptation) factors. It is also affected by dynamic behavior such as the rate of change of temperature.

The present technology takes the complex relationship between environmental factors and comfort into account with the use of personal comfort systems (PCS), that may be integrated into building climate conditioning schemes. Personal comfort systems directly heat and cool occupants or their immediate environments, so they have the potential of fulfilling the thermal comfort preferences of the occupants of a building with great efficiency. Since individual occupants require far less energy to heat and cool than it takes for the entire indoor space, the PCS systems provide individual comfort within a broader range of indoor ambient temperatures (varying over both time and space) with only small amounts of energy. In addition to providing thermal comfort that can be individualized to each occupant, the PCS system can produce HVAC energy savings in buildings.

Because much of the HVAC energy goes into maintaining a narrow range of indoor temperatures, relaxing this temperature range in either the hot or cold direction can lead to an energy reduction at a rate of about 10% per degree C. Energy reduction savings of this magnitude substantially exceed virtually any energy-conserving technology currently available. Such savings can also be obtained with system control reprogramming and without changing the HVAC hardware of the building.

The personal comfort systems described herein treat thermal comfort as a physical-physiological phenomenon and the system devices manipulate perception by stimulating psychophysical effects in the occupant's thermal sensory system. The system devices also affect human thermal sensations by influencing the heat transfer between a human body and its surrounding environment. Although individual comfort requirements will differ due to variation in gender, age, body mass, clothing habits, metabolic rate, and thermal adaptation, the thermal perception and comfort of each occupant will improve with the use of the personal comfort systems and will not be strictly dependent on the ambient temperature.

Heating and cooling different parts of the body is observed to produce different results physiologically and psychologically in humans. The discomfort from a whole-body thermal imbalance may become apparent in heightened sensitivities at a local body part such as the foot or head. For example, cooling the head and warming the feet will create a bigger comfort effect than heating the head and cooling the feet. Only a small amount of energy is needed to heat or cool this body part to restore a satisfactory thermal comfort level.

Embodiments of the PCS devices provide occupant controllable point heating or cooling of thermally sensitive body parts and the ability to produce comfort in ambient temperatures that are above or below the neutral temperatures of the occupant.

Investigations with thermal probe (thermode) arrays suggested that the heating or cooling of a pair of small separated spots would provide the same perceived effect as a large heated area. Warming is felt across an area surrounding each thermode point, as well as across the whole distance between the two warming points.

These heating and cooling spots are preferably supplied by discrete thermal elements, or by linear strips that intersect the body at specific spots. The heating or cooling spots are positioned in place with respect to the body with a support. For example, the support for the point array can be a lower or upper arm band, a wristband, a headband, a sock, a shoe insert, a pad or a necklace and the like. The support provides a spatial component in the in the distribution of heating/cooling spots or strips etc. in the array that create a conscious experience of thermal comfort.

The thermal element spots may be conductive, meaning the body presses against the heating/cooling spot element by gravity or by engaging with a band, etc. Examples could be the seat of a chair with spots built into the chair outer layer, or the wristpad or shoe insole. A thermal necklace might represent a type of band. Also, in some cases small thermal infrared elements might heat spots radiatively from a very close distances from the support. Spot cooling might also be encouraged convectively with micro jets of air.

The spot heating/cooling approach is an efficient means of heating and cooling the human skin because it requires the least power from the electrical source. The heating point source can use radiative or convective heat transfer, as well as conductive heat transfer.

The array of heating or cooling elements placed at designated locations in the support is operably coupled to a controller and power source. In one embodiment, the controller has a wired or wireless input interface that allows the user to control the temperature of the spot heating/cooling elements. The interface may be simply an on-off switch activating the thermal elements to a set temperature or it can be a separate interface device such as a smart phone that allows the user to adjust temperatures, durations and activation and deactivation patterns.

In another embodiment, the array has an optional air or skin temperature sensor that is also connected to the controller. In another embodiment, the system includes a wireless communication output that is configured to communicate with building thermostats or other environment control systems.

Accordingly, the methods and apparatus for applying heating (or cooling) to a portion of a human body part to produce a warm sensation over a larger area than the points where heat is applied. There are three types of heating/cooling approaches and configurations that are preferred, namely, 1) Two-point; 2) Multiple-point; and 3) Switching-point heating/cooling approaches.

In the two-point heating/cooling approach, at least two separated thermal element surfaces (i.e. "spots" or "points") of any shape and size as small as 10 mm diameter are applied to the skin of any body part of the human body. The spot heating, for example, can induce a warm sensation that is localized not only under or near the two heating points, but extends also over the entire skin surface between them. The perception effect extends over a range of distances separating the two points depending on the particular body part (e.g., 7.5 cm for the palm; 25 cm for the back etc.) that is engaging the thermal elements. The two-point extended heating phenomenon allows the body part to be heated more efficiently because heat is applied only to selected points rather than to the entire skin surface area.

With multiple-point heating/cooling, the number of pairs (or other groupings) of heating/cooling thermal element points can be increased to extend the enhanced warm sensation of two-points heating across a larger area of the surface of the body part. For optimal effect, the heating spots are located on the most thermally sensitive areas within a body part. The sensitive areas of a body part may be different for heating than for cooling.

The switching-points heating/cooling approach is used with multiple-point heating/cooling arrays. To optimize the heating effect and minimize the energy requirements, pairs of points in multiple-point heating/cooling arrays can be sequentially activated (e.g., 20 seconds apart), according to different spatial and temporal patterns. This provides extended two-point heating to a larger body area with less power than is required with continually powering the all of the points in the array. The length of time that a pair of thermal element points is activated depends on psychophysiological factors. The apparatus can be tuned for the comfort of a particular user.

When a pair of thermal elements is initially switched from inactive to active mode, it is optimal to maximize power to increase the temperature rise of the element in the switching pairs heating configuration. Following the initial activation, the power can then be gradually lowered.

In all heating pulses, the perception of heating is the strongest at the beginning as the skin temperature changes most rapidly, and subsequently drops off as the rate of change in skin temperature decreases. During the initial period of a step change in temperature, thermal receptor signals are the strongest, as much as 10 times greater than under steady state temperature. This perceptual effect makes switching-points heating more effective than steady-state heating. Similar sensations apply to spot cooling by the contact surfaces.

Accordingly, heating or cooling a body part (e.g. hand, sole, bottom, back, arms) via spot heating rather than whole-area heating, translates into significant power savings. These minimal energy demands also translate into significant reductions in battery size, material and labor costs of the heating device, as well as a reduced chance of "device failure."

In addition to cost and energy savings, the increased warming perception from two-point, multipoint, and switching point stimulation causes a downward adaptation in the individual's neutral skin temperature. The body is induced to heat and cool itself by adjusting its neutral setpoints. For most users, the body experiences an increased thermal warming or cooling perception at any level of heating and cooling power.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of apparatus, system and methods for environmental conditioning incorporating personal comfort systems (PCS) that provide control over the thermal comfort of individual occupants are generally shown. Several embodiments of the technology are described generally in FIG. 1 to FIG. 7 to illustrate the characteristics and functionality of the controllable point heating and cooling devices, methods and systems. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
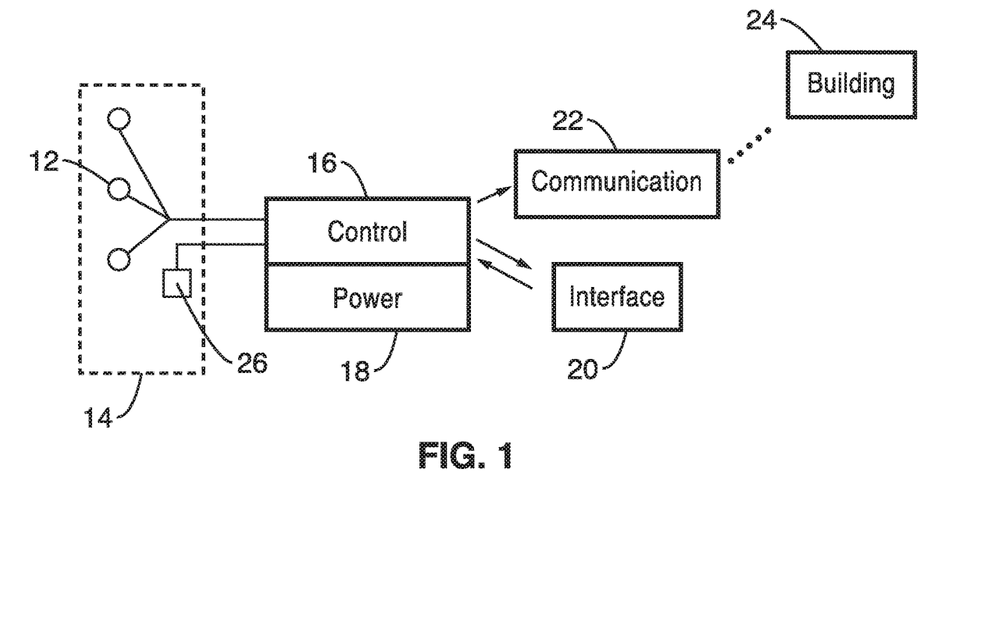
FIG. 1 is a schematic block system diagram of a multi-point heating/cooling array, controller, interface and output according to one embodiment of the technology.

Turning now to FIG. 1, one embodiment of a personal comfort system 10 with an apparatus with multiple heating/cooling elements is shown schematically. The personal comfort system embodiment shown generally in FIG. 1, has a plurality of heating and/or cooling elements 12 that are positioned at designated locations and distances between each other on a support structure 14.

The structure of the support 14 of the elements 12 can have a variety of different forms including, for example, a conductive surface of a seat, bed, armrest, or wrist pad, as well as sleeves, belts, straps, cuffs, collars, pads, inserts, insoles, adhesive patches etc. The support 14 is adapted to engage a body part of the user and position the heating/cooling elements 12 at generally defined locations on the user. For example, the support 14 could be in the form of a tubular upper arm sleeve that will orient the heating/cooling elements 12 of the interior of the sleeve on to the surface of the skin of the arm of the user.

The structure of the support 14 can be tailored for placement on a particular target part of the body and for placement of thermal elements 12 on specific locations on the target. For example, the type of support 14 that is directed to engaging the back or neck of the user can be different than a support directed to an arm or leg. However, in other embodiments, the support structure 14 may be a patch or pad that can be universally applied to any location on the body or engaged by the body.

The thermal (heating/cooling) elements 12 are connected to a controller 16 and a power supply 18 in the embodiment shown in FIG. 1. The thermal elements 12 can be a variety of shapes and surface areas and the size of the elements can be selected based on the identity and size of the body part that the thermal element 12 will engage. For example, the number and size of the thermal elements 12 in a support 14 that engages the upper arm may be smaller than with a support 14 that will engage the back. Thermal elements 12 with round or oval shapes with diameters ranging from between about 10 mm and about 40 mm are preferred. However, the size and shapes of the thermal elements are not limited to these characteristics. The size of the thermal elements can be different depending on the part of the body that is to be engaged by the elements.

The number of thermal elements 12 and the distances between thermal elements may also be optimized. The optimum distances between thermal elements 12 are preferably determined by the maximum distance that will produce a warm or cool sensation over an area between the thermal elements. This will produce the desired thermal effects with the fewest number of thermal elements 12.

The controller 16 is configured to actuate each of the heating/cooling elements 12 to a designated temperature or range of temperatures. In one basic embodiment, the controller 16 provides a simple on/off switch control that actuates the heating/cooling elements 12 to preset temperatures and durations or until the switch is turned off.

In another embodiment, the controller 16 permits the user to vary the temperature of the heating/cooling thermal elements 12 to a desired temperature within a range of temperatures.

The hot or cold temperatures that are produced by the thermal elements 12 are within a range that is centered at the normal human body thermal neutral temperature but not so extreme that burning or freezing sensations are created by the thermal elements.

Typically, different thermal stimuli may feel hot or cold depending on how they compare with the current skin temperature of the occupant. Physiological neutral temperature is around 91° F. (33° C.) in a normal room temperature of 68° F. (20° C.) environment and the body maintains a temperature of about 98° F. (37° C.) in these conditions.

Accordingly, the thermal elements preferably heat the skin to no more than about 109° F. (43° C.) at the skin surface, which is the threshold for the pain receptor. The thermal element itself might need to be hotter. For example, its temperature might need to be 45° C. to about 48° C. if there is a covering layer of fabric, or, in the case of the insole, the person would be wearing a sock between the skin and the thermal heating element. The lowest heating temperature at the skin preferably be about 36° C., which is above almost all normal skin temperatures.

The lowest cooling spot temperature at the skin would be about 18° C. and the highest cooling skin temperature would be around 28° C. This should be the range of adjustment. 25° C. is the peak cool receptor firing temperature. The comfortable range for a given spot or time depend on the body part, the person's body temperature, and the amount of clothing insulation over the skin.

Although these temperature ranges are preferred, the thermal elements 12 may be brought to any temperature or range of temperatures that will produce the heating or cooling effect between elements and the overall thermal comfort of the user.

In a further embodiment, the controller 16 includes a processor and programming residing in a non-transitory computer readable medium that is executable by the computer processor and configured to actuate each of the heating/cooling elements 12 to a designated temperature or range of temperatures for a programmed sequence and duration. In this embodiment, the controller 16 includes a processor, memory, and application software code. The processor can be any suitable conventional processor. The memory may include any suitable conventional RAM type memory and/or ROM type memory with associated storage space for storing the application programming code.

The controller 16 may also have an optional interface 20 to allow user interaction with the controller or programming of the controller to activate and set temperatures and times of heating/cooling element 12 activity. The interface 20 may be wired or wireless interfaces. Examples of wireless interfaces 20 include smartphones, tablet computers, laptop computers, and desktop computers. These interfaces may also assist in programming the controller 16 as well as compile and record usage statistics, in one embodiment.

The controller 16 may also have an optional communications link 22. The control interface 20 can also be connected to the controller 16 through the communications link 22. The communications link 22 of controller 16 can be a wired communications interface or a wireless communications interface such as a cellular communications interface, a Wi-Fi communications interface, a near field communications interface, an infrared communications interface, or a Bluetooth communications interface.

In the embodiment shown in FIG. 1, the controller 16, through communications link 22, may be in communication with building computer servers or thermostat 24 and integrated into building environmental control schemes. Building servers 24 with environmental control programming and thermostats controlling the air conditioning may be provided in a client-server configuration and may include standalone servers, cluster servers, networked servers, or servers connected in an array to function like a large computer.

In one embodiment, the support 14 also has one or more optional sensors 26, such as air temperature or humidity sensors, that are connected to the controller 16. The data from the sensors 26 can processed or simply transmitted through the communications link 22 to a remote device such as a building server 24. Multiple personal comfort system devices that are incorporated into the building environmental control system can provide sensor data such as temperatures from users in many different locations in the building and conditioning zones and this information can be used in controlling the building air conditioning. Device activity data from user devices can also provide feedback to the environmental control system about specific occupant comfort and identify trends and ranges of temperatures in zones and rooms.

According to embodiments of the technology, heat or cold is applied to portions of a human body part to produce a warm or cool sensation over a larger area than that to which the heat or cold is directly applied.

Figure 2:
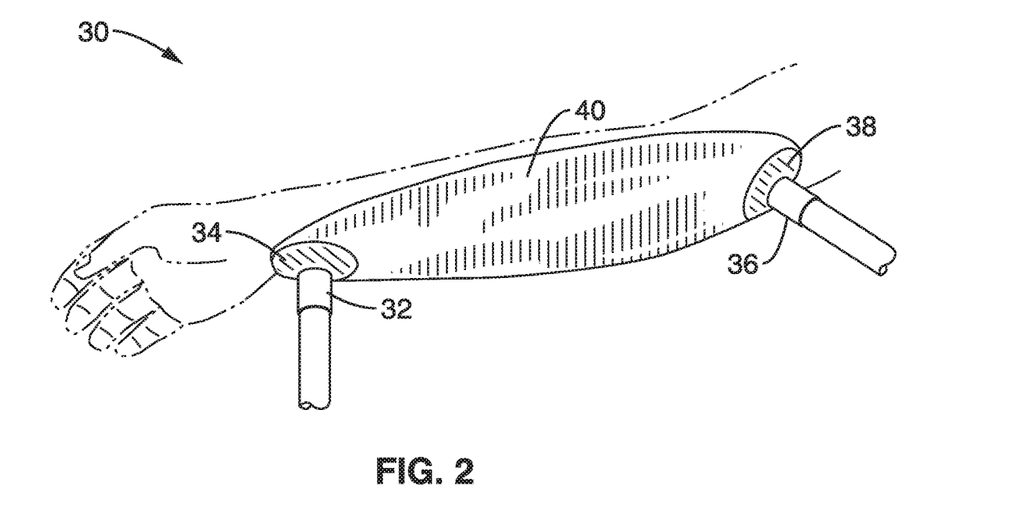
FIG. 2 is a schematic diagram of a two thermal (heating/cooling) thermal element points applied to the arm of a user illustrating sensory infilling distances for two heating/cooling points on the forearm.

Referring now to FIG. 2, the general functional aspects of the two-point heating/cooling scheme 30 embodiment are illustrated.

The apparatus and system utilize the psychophysiological sensing called "thermal referral" or "filling-in." It has been observed that when at least two separated heating points of any shape and of a size as small as about 10 mm are applied to the skin of a human body part, a warm sensation is induced that is localized not only under the two heating points, but also extends over the entire skin between the points (even though this area is not directly exposed to any heating source). As illustrated in FIG. 2, the heating/cooling point 32 will produce a localized hot or cold thermal area 34 surrounding the heating/cooling point 32. A similar localized thermal area 38 will be produced immediately surrounding the heating/cooling point 36. However, the area between the two heating/cooling points will experience an induced warm or cool sensation area 40 of sensation that will feel to the user as though it is being heated or cooled even though the area is not directly engaging either of the heating/cooling points 32, 36.

In another example, thermal stimulators are applied to each of the middle three fingers of one hand. When the outer two stimulators are actuated to be warm or cold relative to the skin temperatures and the central (neutral) stimulator is not actuated, the central stimulator is also perceived to be cold or warm.

The sensation intensity between the two points in sensation area 40 may be less strong than the sensations 34, 38 experienced at the two points, or they may be equally strong. The distances between the two points can be varied and optimized to produce the desired effect on selected parts of the body. To induce the desired effect, for example, the distance between the two points can vary largely (e.g., 7.5 cm for the palm; 25 cm for the back). Table 1 illustrates infilling distances between the two warm stimulus points of 14 mm diameter.

Thermal comfort is a subjective valuation which can display large differences among individuals who are exposed to the same ambient temperatures and environmental conditions. To increase the percentage of occupant comfort, thermal referral formation has been incorporated into the devices and methods for providing environmental comfort to a user through heating or cooling points producing sensation areas in various parts of the body. The heating/cooling (h/c) is applied in multiple "points" spread across the skin, rather than through heating or cooling entire surfaces of the body. The comfort level of the user is improved with the system without changing ambient temperatures or conditions.

Depending on the size of the body part to be heated/cooled, in another embodiment, referred to as "multiple-points heating," the number of heating points can be increased in pairs or groups to spread the enhanced thermal sensation in additional directions across the body part.

The location of each heating/cooling point in relation to points of a body part can also be selected with the design of the support. For example, a band or cuff of a resilient material can be used to orient the heating/cooling points over locations and concentrations of thermoreceptors or other heat or cold sensitive locations on the body. Strategic placement of an optimum number of spatially oriented heating/cooling points at sensitive locations can provide improved comfort levels without raising the temperature of either the body or the ambient temperature.

The thermal element points can be made of electrical resistance devices, or thermoelectric (TE) devices, or of any other similar system providing surface contact heating or cooling. In addition to contact heating of the skin, it will be appreciated that the point heating stimuli can also be small sources of radiant heating. Furthermore, the technology described above can also be extended to spot cooling of the skin by contact surfaces or by small jets of air, for example.

It can be seen that thermal sensation areas can be created on different parts of the body by spot heating or cooling with thermal elements engaging the body by a variety of support designs adapted to the body locations. For example, shoe insoles can be designed with point heating or cooling elements configured to engage the foot of the user at different locations on the feet.

Figure 3:
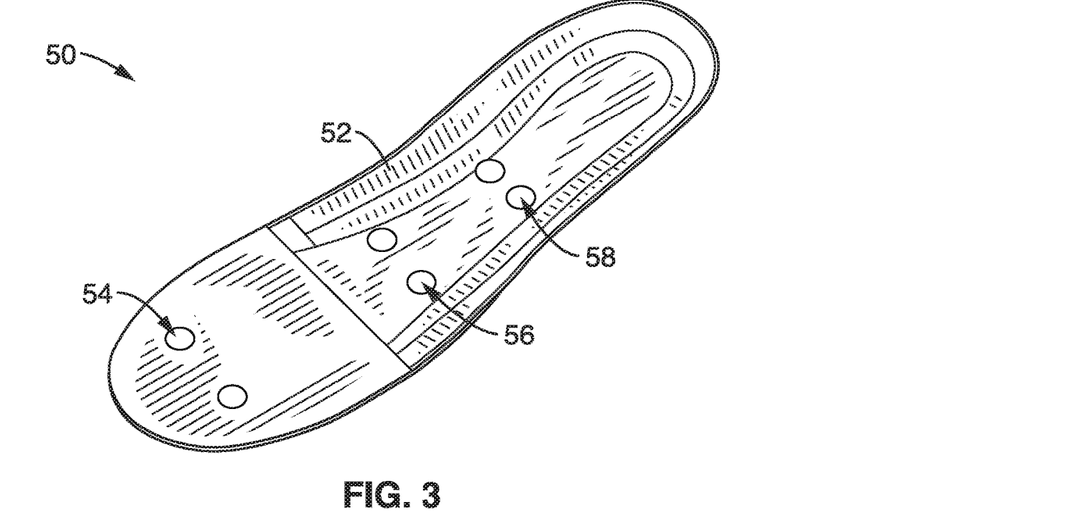
FIG. 3 is a schematic diagram of a heated shoe insole with three pairs of thermal points according to one embodiment of the technology.

In the embodiment shown in FIG. 3, an insole design 50 is shown with an insole support 52 with one pair 54 of heating elements under the toes and two pairs 56, 58 of elements located along the foot under the arch. In this illustration, the thermal elements 54 under the toes and arch 56, 58 can be heated or cooled to a set temperature. However, the thermal elements can also be heated/cooled in pairs or individually and for different durations.

For example, one embodiment of the insole built with 6 heating points shown FIG. 3 has only one pair of thermal elements actively heated at a time. The three pairs of elements are separately and sequentially heated every 20 seconds, for example. The pair pattern may begin with the toe elements and proceed to the first arch elements to the second arch elements and back to the toe elements.

Typically, the thermal elements in the insole supports engaging each foot will be heated or cooled to approximately the same temperature. However, the apparatus in each insole can be tuned to provide pairs of thermal elements at a range of different temperatures in other embodiments. The thermal elements may also be in triplets or other clusters as well as in single positions in the insole support 52.

Figure 4:
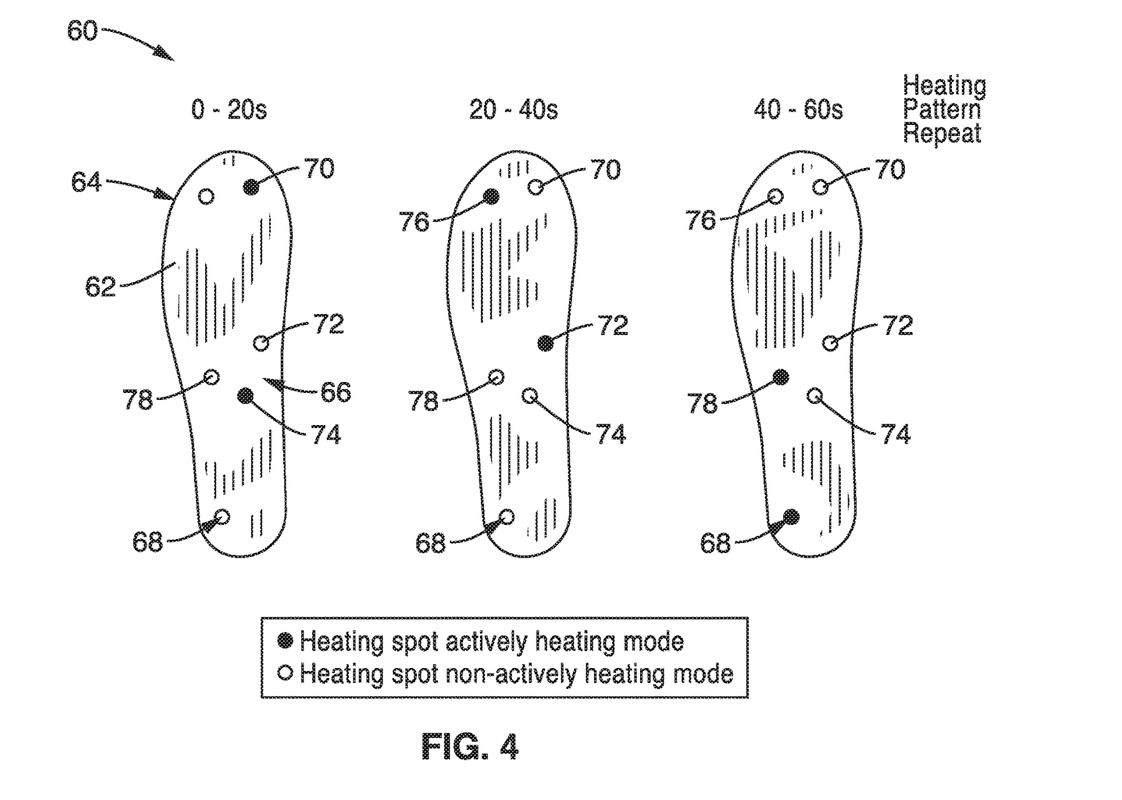
FIG. 4 is a schematic diagram of a heated/cooled insole with multiple thermal points illustrating temporal actuation of the various thermal points in a programmable pattern of actuations, deactivations and durations.

To optimize the heating/cooling effect and minimize energy requirements, in one embodiment, pairs (or other groupings) of points in multiple-point heating/cooling arrays can be sequentially activated for short time periods (e.g., 20 seconds), according to different patterns. This is referred to as "switching-points" heating or cooling and is illustrated in FIG. 4 in the context of an insole support. However, the approach can be applied to any support structure and body part.

FIG. 4 depicts an insole 62 with three groupings of thermal elements with different numbers of elements in each group and showing a pattern of actuation of specific thermal elements during three different time periods, beginning from left to right. The insole configuration in this illustration has a first group 64 of two thermal elements 70, 76, and a second group 66 of three thermal elements in the arch and a third group with a single element 68 at the heel of the insole support 62. In the first period, (0-20 s), the thermal element 70 at the toe and thermal element 74 at the arch are active and the other elements of the insole are inactive. Activation of these point elements creates thermal sensations between the two points 70, 74, in this illustration. During the second time period (20-40 sec), the thermal elements 70, 74 that were active in the first phase are switched off and a toe thermal element 76 and a different arch element 72 are actuated in the second phase (20-40 sec). The third actuation time period, taking place at 40-60 sec, shows an arch thermal element 78 and the heel thermal element 68 are activated and all other elements are deactivated for this period of time.

This switching point scheme 60 provides the extended two-point heating to a larger body area with less power than continually powering the all the points in the array. The amount of energy required to activate two points will provide warmth sensation over the larger surface area of the multiple-point array. Although two thermal elements were activated during each time, more than two thermal elements can be activated simultaneously. For example, one element from each group such as a toe element, an arch element and a heel element can be activated for a selected period of time.

Switching between heating points by the controller as illustrated in FIG. 4 creates changing temperatures (pulses) in the heating surfaces and in the skin temperature beneath them. Thermoreceptors in the skin can be as much as ten times more sensitive to changing skin temperatures than to sensing a steady state temperature. Even at a lower average skin temperature, the sensation of warming from pulse heating can be greater than that of steady state heating. This demonstrates how switching-point heating with its very low inherent energy levels and lower average skin temperatures can be effective.

The optimal length of time of a heating pulse may also vary, but the earliest perception of heating is observed to be the strongest, dropping off as the rate of change of skin temperature decreases. Therefore, a repeating heating/cooling pattern can be particularly effective in producing beneficial thermal sensations and overall comfort. To further maximize the heating/cooling effect, the thermal spots are preferably located on the most thermally sensitive areas within a body part. Accordingly, spatial and temporal point heating/cooling locations and activation duration and sequence can be optimized for a specific body part.

It is also noted that the use of point heating causes the body to adapt its neutral skin temperature to a cooler value. Because of this effect, thermal warmth is perceived in cooler ambient temperatures so long as point heating is present in small portions of the body.

Beneficially, heating a body part (e.g., hand, sole, bottom, back) via small spots rather than whole-area heating uses significantly less power. For example, heating the human palm via spot heating can be accomplished by a two-points heating device drawing only 0.5 Watts to 1 Watts. Such minimal energy demands also translate into significant reductions in battery size, material and labor costs when producing a personal comfort system (PCS) heating device (e.g. thermoelectric heating devices on a heated chair seat).

Because the use of spot heating causes the body to adapt its neutral skin temperature downward; comfort is perceived in cooler ambient temperatures when point heating is present. Buildings maintained at cooler ambient temperatures can save large amounts of HVAC energy; orders of magnitude greater than the power used by the PCS to provide the point heating.

Although the thermal elements are normally permanently fixed to the support, in one embodiment, the positions of the thermal elements can be adjusted by the user to optimize the placement of the elements on the body parts. In one embodiment, the heating elements may be adjustable along sliders or reversibly fixed with hook and loop or other fasteners and can be dynamically positioned and controlled in various combinations.

Figure 5:
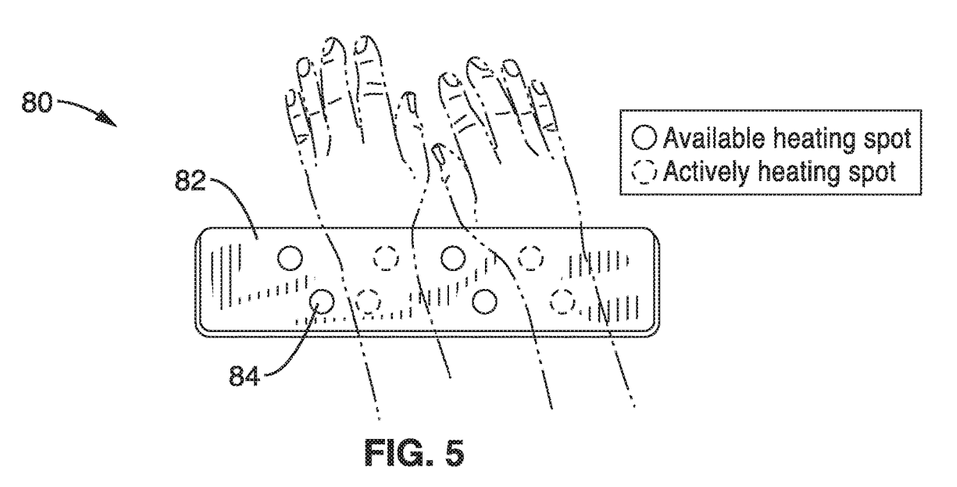
FIG. 5 is a schematic diagram of an embodiment of a heated wrist-pad with a pattern of thermal element points that engage the hands/wrists in pairs of points during typing or other use.
Figure 6:
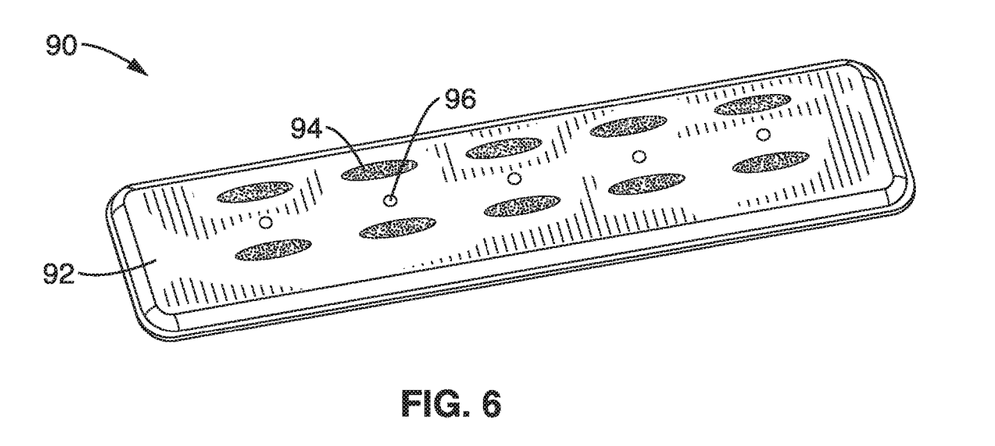
FIG. 6 is a schematic diagram illustrating an alternative embodiment of a wrist-pad heating device with spaced parallel lines of ellipse shaped thermal points according to the technology.

In other embodiment, the support with the thermal elements is not worn or reversibly coupled to the body, rather the body part is placed on the thermal elements of the support to achieve the thermal sensory effect. For example, a support 80 in the form of a computer wrist pad 82 with eight thermal heating points 84, represented by open solid circles, is shown in FIG. 5. In this case, one or both hands and/or wrists of the user engage the wrist pad 82 and thermal elements 84. In one embodiment, only two thermal element spots 84 that are in contact with the two wrists are actively heated, represented by the two dash-line circles. In another embodiment, two thermal elements 84 under each hand or wrist are activated providing thermal transfer and thermal sensitivity to both wrists/arms is provided.

In a variation of the embodiment of FIG. 5, the thermal elements can be larger than points. In the apparatus 90 shown in FIG. 6, a wrist pad with 10 heating points, represented by paired ovals 94 positioned in parallel lines along the length of the pad 92. As described previously, each oval is connected to a power source and to a controller (not shown) within the body of the pad 92. The oval thermal elements 94 organized in parallel rows are activated. The thermal elements 94 engage portions of the wrist/hands of the user when they are placed on the pad while typing. In one embodiment, the body of the pad 92 also has pressure sensors 96 to identify the location of the hands or wrists of the user, allowing the controller to activate only the thermal elements 94 under the hands/wrists of the user.

Figure 7:
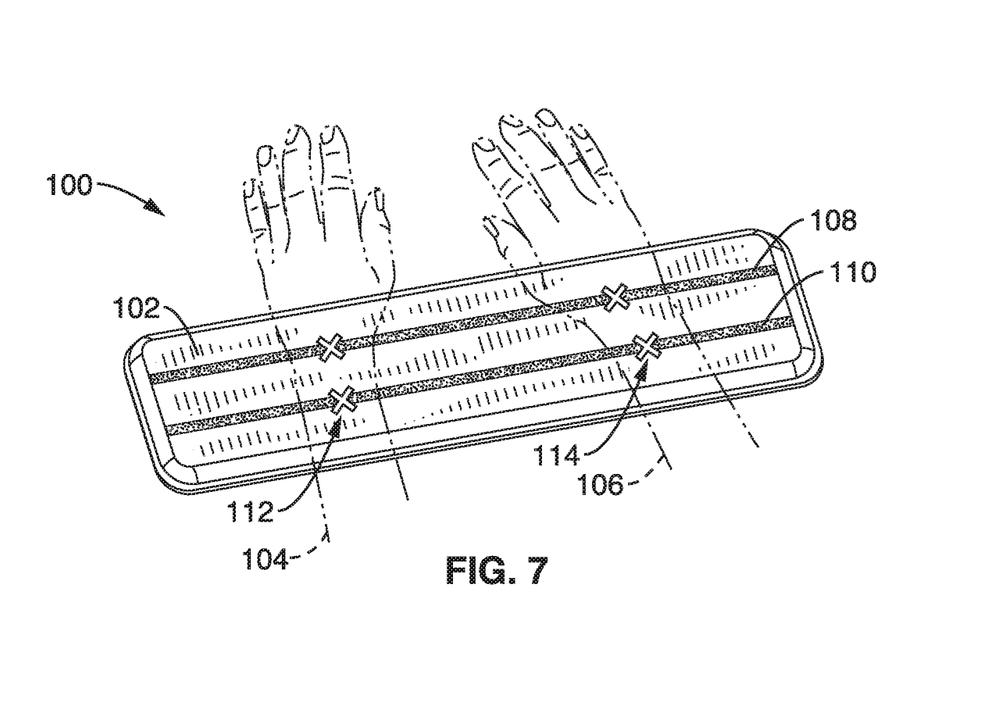
FIG. 7 is a schematic diagram of an alternative embodiment of a wrist-pad heating device with spaced parallel thermal strips that engage the wrists and palms of the hands.

Similarly, in an alternative embodiment shown in FIG. 7, the apparatus 100 has a wrist pad 102 with two linear heating strips along the length of the wrist pad 102. The left wrist of arm 104 and the right wrist of arm 106 engage the upper strip 108 and lower strip 110 during use of the wrist pad 102. In one embodiment, only the two spots 112 of the left and the two spots 114 of the right wrists that are in contact with the top 108 and bottom 110 strips are actively heated by the strips, represented by two X marks. In another embodiment, the upper strip 108 and the lower strip 110 are continuously heated or cooled to a temperature or range of temperatures set by the controller and user.

It will be appreciated that heating or cooling a body part (e.g., hand, sole, bottom, back) by an array of points uses less power than a whole-area source. The reduced energy demands translate into significant reductions in battery size, and in material and labor costs of the heating/cooling device. Because spot heating and cooling sources operate at higher temperature differences from the skin than do area sources, they create a stronger perceived thermal sensation for the same power consumption. The temperature pulses in switching-points heating and cooling are also perceived more strongly than steady-state heating and cooling and are therefore more effective for a given power consumption.

The technology described herein may be better understood with reference to the accompanying examples, which are intended for purposes of illustration only and should not be construed as in any sense limiting the scope of the technology described herein as defined in the claims appended hereto.

Example 1

To demonstrate the operational principles of the apparatus and methods for two-point and multi-point spot heating and cooling, insoles with spot heating elements were fabricated and evaluated. In this example, an insole heated by 6 heating points centered near the arch of the foot of the user. More heating spots were located near the center of the sole and at the base of the toes because those areas are more sensitive to heating or cooling. Body part sensitivities increase with observed discomfort from whole-body thermal imbalance. Only a small amount of energy is needed to heat or cool a body part to restore comfort. In this example, the foot was tested with an insole with 6 surface heating points which was powered in many pair combinations. Infrared images of the surface temperatures generated by the heating points at different settings of the test insoles were taken.

The heating was supplied by electrical resistance devices in some tests and cooling was supplied by thermoelectric (TE) devices as the thermal elements in other tests. The point surface thermal elements of different shapes and sizes were tested demonstrating that the thermal elements are not limited to any one shape or size and the size can be as small as 10 mm.

To further optimize the heating effect with minimum energy, in one test the 6 heating spots were arranged into 3 pairs, with the distance between the two points in a pair being about half the length of the foot. The three pairs were heated at different times sequentially so at any time only 1 pair was actively heating. The cycle time for a pair was approximately (e.g.) 20 seconds. Other cycle times were also tested. The initial power when a pair was switching from inactive to active heating mode should be greater (e.g., 0.6 Watts/spot) to increase the heating speed for the first (e.g.) 8 seconds. Following the initial activation, the power was ramped down to (e.g.) 0.3 Watts/spot. This pattern continued as long as the insole was heating the test subject's foot. Control over the timing and sequence of actuation of the thermal elements of the insole at different ambient temperatures in relation to perceived comfort of the test subjects was demonstrated.

Example 2

To further demonstrate the operational principles of the apparatus and methods, several wrist pads with thermal elements of different shapes located at different points along the length were evaluated. In one test prototype, the wrist pad was heated/cooled by 8 to 10 points. These thermal elements were grouped in 4 or 5 pairs. Thermal elements with several different shapes and different sizes (as small as 5 mm) were tested.

In one evaluation, the initial power delivered to a pair of thermal elements switching from inactive to active heating mode was greater (e.g., 0.6 Watts/point) to increase the heating speed. Following the initial activation, the power was then gradually lowered (e.g. 0.3 Watts/spot). When hands are moving, only one pair (two points) under each wrist is heated.

The technology was also tested for point cooling by contact surfaces. The cooling sensation between two cooling points was observed to be weaker than the warm sensation between two warming points. Modification of the distances between thermal elements improved the produced sensations and overall comfort.

From the description herein, it will be appreciated that that the present disclosure encompasses multiple embodiments which include, but are not limited to, the following:

1. An apparatus for providing thermal comfort, the apparatus comprising: (a) a multiple point thermal array with at least two spaced apart thermal elements capable of heating or cooling at one or more temperatures; (b) a thermal element support configured to orient the thermal elements of the array to engage a surface of the skin of a human body part; (c) a controller operably coupled to the thermal elements and to a power source, the controller configured to control activation and duration of activity of the thermal elements; (d) wherein a warm or cool sensation is induced by the activity of the thermal elements that is localized not only under the thermal elements, but also over an entire skin area between the thermal elements, thereby producing thermal comfort.

2. The apparatus of any preceding or following embodiment, wherein the thermal elements produce a heat transfer selected from the group consisting of radiative heat transfer, convective heat transfer and conductive heat transfer.

3. The apparatus of any preceding or following embodiment, wherein the thermal element support is a support selected from the group of supports consisting of sleeves, belts, straps, cuffs, collars, pads, inserts, insoles and adhesive patches.

4. The apparatus of any preceding or following embodiment, wherein the thermal element support further comprises: a plurality of thermal elements separated by a maximum distance between elements that will produce a warm or cool sensation between thermal elements; wherein the body part of a user experiences increased thermal warming or cooling perception at any level of heating and cooling power of the thermal elements.

5. The apparatus of any preceding or following embodiment, wherein the controller further comprises: (a) a control interface; (b) a processor configured to receive input from the control interface; and (c) a non-transitory memory storing instructions executable by the processor; (d) wherein the instructions, when executed by the processor, perform steps comprising: (i) controlling activation of each thermal element of the thermal array; (ii) controlling a duration of activation of each thermal element; (iii) controlling a temperature of each thermal element; and (iv) controlling a rate of temperature change of each thermal element; (e) wherein the body part of the user is induced to heat and cool itself by adjusting neutral setpoints in response to the activity of the thermal elements.

6. The apparatus of any preceding or following embodiment, wherein the instructions when executed by the processor further perform steps comprising: designating multiple groups of two or more thermal elements in the array for simultaneous activation; activating and deactivating the designated groups of thermal elements in the array according to a pattern; and controlling the duration of thermal element activation of each group; wherein dynamic changes of skin temperature during the patterned activations is perceived more intensely by a user than a steady state temperature.

7. The apparatus of any preceding or following embodiment, wherein the instructions when executed by the processor further perform steps comprising: applying full power to the thermal elements upon initial activation; and gradually lowering the power to the thermal elements after initial activation for a set duration.

8. The apparatus of any preceding or following embodiment, further comprising a temperature sensor mounted to the support with an output connected to the controller.

9. The apparatus of any preceding or following embodiment, wherein the controller further comprises a communications module adapted to transmit and receive transmissions from an external device.

10. The apparatus of any preceding or following embodiment, wherein the control interface comprises a smartphone.

11. A method for producing thermal sensations in the body, the method comprising: (a) heating or cooling a first skin surface of a body part with a first thermal element; and (b) heating or cooling a second skin surface of the body part with a second thermal element separated from the first thermal element by a distance; (c) wherein a warm or cool sensation is induced that is localized not only under the two thermal elements, but also over an area between the two thermal elements.

12. The method of any preceding or following embodiment, wherein the thermal elements produce a heat transfer selected from the group of radiative heat transfer, convective heat transfer and conductive heat transfer.

13. The method of any preceding or following embodiment, further comprising: identifying thermally sensitive areas of a body part; and heating or cooling points on the identified thermally sensitive areas with the first and second thermal elements.

14. The method of any preceding or following embodiment, further comprising: identifying a maximum distance between the first thermal element and the second thermal element that will produce a warm or cool sensation over an area between the thermal elements; and locating thermal elements at the identified maximum distances.

15. The method of any preceding or following embodiment, further comprising: heating or cooling a third skin surface of the body part with a third thermal element separated from the first thermal element by a distance and the second thermal element by a distance; wherein heating or cooling separated points with each thermal element on the surface of a human body part to induce a warm or cool sensation in an area between the points.

16. A method for producing thermal comfort in a human body, the method comprising: (a) providing a multiple-point array of thermal elements configured to engage skin surfaces of a body part controlled by a controller; (b) controlling activation, duration and temperature of each thermal element with the controller; and (c) heating or cooling skin surfaces of a body part with actuation of the thermal elements; (d) wherein heating or cooling at least two separated points on the surface of a human body part will induce a warm or cool sensation at the points and over an area between the points; and (e) wherein point heating or cooling are used rather than whole-area heating or cooling to cool down or warm up the body part.

17. The method of any preceding or following embodiment, further comprising: identifying thermally sensitive areas of a body part; locating the array of thermal elements on the identified thermally sensitive area; and heating or cooling the thermal elements on points on the identified thermally sensitive areas.

18. The method of any preceding or following embodiment, further comprising: pairing thermal elements in the array; and sequentially switching pairs of thermal elements in the multiple-point array of thermal elements on and off at different times, according to different patterns.

19. The method of any preceding or following embodiment, further comprising controlling the duration of the on and off activation of the thermal elements.

20. The method of any preceding or following embodiment, further comprising: grouping thermal elements in the array; and sequentially switching thermal elements of the group in the multiple-point array of thermal elements on and off at different times, according to different patterns; and controlling the duration of the on and off activation of the thermal elements.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

What is claimed is:

1. An apparatus for providing thermal comfort, the apparatus comprising:
    (a) a multiple point thermal array with at least two spaced apart thermal elements capable of heating or cooling at one or more temperatures;
    (b) a thermal element support configured to orient said thermal elements of the array to engage a skin surface of a user's body part;
    (c) a controller operably coupled to the thermal elements and to a power source, said controller configured to control activation and duration of activity of the thermal elements;
    (d) wherein a warm or cool sensation is induced by the activity of the thermal elements that is localized not only under the thermal elements, but also over an entire skin area between the thermal elements, thereby producing thermal comfort;
    (e) wherein said controller further comprises:
        (i) a control interface;
        (ii) a processor configured to receive input from the control interface; and
        (iii) a non-transitory memory storing instructions executable by the processor;
        (iv) wherein said instructions, when executed by the processor, perform steps comprising:
            (1) controlling activation of each thermal element of the thermal array;
            (2) controlling a duration of activation of each thermal element;
            (iii) controlling a temperature of each thermal element; and
            (3) controlling a rate of temperature change of each thermal element;
    (f) wherein the user's body part is induced to heat and cool itself by adjusting neutral setpoints in response to the activity of the thermal elements.

2. The apparatus of claim 1, wherein said thermal elements produce a heat transfer selected from the group consisting of radiative heat transfer, convective heat transfer and conductive heat transfer.

3. The apparatus of claim 1, wherein said thermal element support is a support selected from the group of supports consisting of sleeves, belts, straps, cuffs, collars, pads, inserts, insoles and adhesive patches.

4. The apparatus of claim 1, wherein said thermal element support further comprises:

a plurality of thermal elements separated by a maximum distance between elements that will produce a warm or cool sensation over an area between the thermal elements;

wherein the user's body part experiences increased thermal warming or cooling perception at any level of heating and cooling power of the thermal elements.

5. The apparatus of claim 1 wherein said instructions when executed by the processor further perform steps comprising:

designating multiple groups of two or more thermal elements in the array for simultaneous activation;

activating and deactivating the designated groups of thermal elements in the array according to a pattern; and controlling the duration of thermal element activation of each group;

wherein dynamic changes of skin temperature during the patterned activations is perceived more intensely by a user than a steady state temperature.

6. The apparatus of claim 1, wherein said instructions when executed by the processor further perform steps comprising:

applying full power to the thermal elements upon initial activation; and gradually lowering the power to the thermal elements after initial activation for a set duration.

7. The apparatus of claim 1, further comprising a temperature sensor mounted to the support with an output connected to the controller.

8. The apparatus of claim 1, wherein said controller further comprises a communications module adapted to transmit and receive transmissions from an external device.

9. The apparatus of claim 1, wherein the control interface comprises a smartphone.

* * * * *